US010238818B2

(12) United States Patent
Griffiths et al.

(10) Patent No.: US 10,238,818 B2
(45) Date of Patent: Mar. 26, 2019

(54) SURGICAL SPRAY INSTRUMENT

(71) Applicant: ALESI SURGICAL LIMITED, Cardiff (GB)

(72) Inventors: Dominic Griffiths, Cardiff (GB); Nicholas Evans, Cardiff (GB); Peter Bannister, Cardiff (GB); Neil Warren, Cardiff (GB); Francis Kweku Egyin Amoah, Cardiff (GB)

(73) Assignee: ALESI SURGICAL LIMITED, Cardiff (GB)

(*) Notice: Subject to any disclaimer, the term of this patent is extended or adjusted under 35 U.S.C. 154(b) by 139 days.

(21) Appl. No.: 15/432,217

(22) Filed: Feb. 14, 2017

(65) Prior Publication Data
US 2017/0216537 A1 Aug. 3, 2017

Related U.S. Application Data

(63) Continuation of application No. PCT/GB2015/052368, filed on Aug. 14, 2015.

(30) Foreign Application Priority Data

Aug. 15, 2014 (GB) .................................. 1414536.1

(51) Int. Cl.
A61M 11/02 (2006.01)
B05B 5/03 (2006.01)
(Continued)

(52) U.S. Cl.
CPC ............. A61M 11/02 (2013.01); A61B 34/20 (2016.02); A61M 13/00 (2013.01); A61M 15/02 (2013.01);
(Continued)

(58) Field of Classification Search
None
See application file for complete search history.

(56) References Cited

U.S. PATENT DOCUMENTS 4,040,426 A     8/1977  Morrison
5,571,126 A  *  11/1996  Dorsey, III ........ A61B 17/3203
                                                    606/167
(Continued)

FOREIGN PATENT DOCUMENTS

CN      103611206 A      3/2014
DE    202013104123 U1    9/2013
(Continued)

Primary Examiner — Brian T Gedeon
(74) Attorney, Agent, or Firm — Joseph C. Zucchero; Carolyn S. Elmore; Elmore Patent Law Group, P.C.

(57) ABSTRACT

A surgical spray instrument is disclosed comprising a main body connectable to a transfer tube; a propellant actuator for selectively releasing propellant from the main body and along the transfer tube and out through a distal end thereof. An ion emitter is arranged along the tube, the ion emitter having an ion emission zone. This enables the directed and concentrated delivery of therapeutic, pharmacological and diagnostic agents to tissues inside or outside of the body. There is further disclosed a surgical assembly for enabling uniform deposition of a particulate material to a surface of an intracorporeal cavity of a patient. The surgical assembly comprises an ion emitter; a dispenser having an outlet locatable within the cavity and for dispensing the particulate material therefrom, and a processor for determining a location of the ion emission zone of the ion emitter in dependence upon the position of the outlet of the distributor within the cavity to provide for the uniform deposition.

10 Claims, 6 Drawing Sheets

(51) Int. Cl.
*A61B 34/20* (2016.01)
*A61M 13/00* (2006.01)
*A61M 15/02* (2006.01)
*B05B 5/053* (2006.01)
*B05B 5/08* (2006.01)
*B05B 5/12* (2006.01)

(52) U.S. Cl.
CPC ............... *B05B 5/03* (2013.01); *B05B 5/032* (2013.01); *B05B 5/0537* (2013.01); *B05B 5/087* (2013.01); *A61B 2218/003* (2013.01); *B05B 5/12* (2013.01)

(56) References Cited

U.S. PATENT DOCUMENTS

| | | | |
|---|---|---|---|
| 6,079,413 | A | 6/2000 | Baran |
| 6,302,331 | B1 | 10/2001 | Dvorsky et al. |
| 6,905,496 | B1 | 6/2005 | Ellman et al. |
| 8,303,531 | B2 * | 11/2012 | Sharratt ................ A61M 31/00 604/24 |
| 8,470,296 | B2 * | 6/2013 | Dees .................... A61K 31/352 424/1.85 |
| 8,920,849 | B1 | 12/2014 | Callison et al. |
| 2004/0195403 | A1 | 10/2004 | Atterbury et al. |
| 2005/0150491 | A1 | 7/2005 | Chen |
| 2009/0088700 | A1 | 4/2009 | Imbayashi |
| 2012/0067212 | A1 | 3/2012 | Warren et al. |
| 2012/0172874 | A1 | 7/2012 | Fischer et al. |
| 2013/0287962 | A1 | 10/2013 | Deng et al. |
| 2014/0074090 | A1 | 3/2014 | Lam et al. |

FOREIGN PATENT DOCUMENTS

| | | |
|---|---|---|
| EP | 0740926 A2 | 11/1996 |
| EP | 1929969 A2 | 6/2008 |
| FR | 1253788 A | 2/1961 |
| GB | 2128900 A | 5/1984 |
| GB | 2327895 A | 8/1997 |
| JP | 2009273694 A | 11/2009 |
| JP | 20100046418 A | 3/2010 |

* cited by examiner

SURGICAL SPRAY INSTRUMENT

This invention relates to a surgical spray instrument, in particular a surgical spray instrument capable of influencing the directionality of spray particles emitted therefrom to a desired surgical site.

There are many surgical applications whereby it is necessary to introduce particles to a surgical site which may be intracorporeal or extracorporeal. The particle type can vary greatly depending on the application. For example, the particles may be dye particles that are to be administered for the characterisation of internal tissues, for example in Chromoendoscopy. Alternatively, the particles may have a therapeutic effect, for example a haemostatic agent that is commonly used to help vascular clotting example in the case of an upper gastrointestinal (GI) bleed.

For intracorporeal delivery, each of these particle types are usually passed within the body via a tube that enables transfer of the particles as a suspension or aqueous solution from an external position to an internal position within the body of the patient to be treated or observed. To improve the transfer of the particles, they may be propelled by means of a pressurised fluid, for example an aqueous solvent, air or $CO_2$. However, once the particles are released inside the patient they can disperse and become suspended in a local atmosphere and consequently only some of the particles may come into contact with the desired tissue site.

Whilst it is possible to optimise the contact of the particles with the desired site by minimising the separation between the tube outlet and the site, this can at times be difficult or impossible for the surgeon to achieve.

Further, higher pressure fluids may be used to insert the particles in the patient, however if the spray is too forceful it can cause further complications or trauma to the patient.

Therefore, the present invention and its embodiments are intended to address at least some of the above described problems and desires. In particular, it facilitates the directionality of the propellant expelled from the instrument to the intracorporeal site of interest in a reproducible and reliable manner, thereby optimising the contact of the particles with the site. The use of this method may also be used to increase the transfer of the molecule of interest from within an aqueous suspension to the patient tissue, thereby increasing the likely absorption of the molecule into the tissue.

According to an aspect of the invention there is provided a surgical spray instrument which comprises:
- a main body connectable to a transfer tube;
- a propellant actuator for selectively causing particulate material contained in a propellant to pass along the transfer tube and out through a distal end thereof; and
- an ion emitter arranged along the tube, the ion emitter having an ion emission zone.

The surgical spray instrument is for causing directivity of spray particles emitted therefrom to a desired surgical site. Along the transfer tube may mean the ion emitter is positioned to extend within the bore of the tube or adjacent to the tube in an external position.

The ion emission zone may be projectable from the distal end of the transfer tube. This provides an unobstructed spray effect and improved directionality.

The ion emission zone of the ion emitter may be moveable between a stowed position and an operative position.

In the stowed position the ion emission zone of the ion emitter may be retracted within the transfer tube.

In the operative position the ion emission zone of the ion emitter may be projected from the distal end of the transfer tube. The ion emitter therefore may extend past the end of the transfer tube.

A propellant actuator may deploy the ion emission zone of the ion emitter.

An ion emitter actuator may actuate deployment of the ion emitter from the stowed position to the operative position.

A further actuator may be included to actuate the emission of ions from the ion emission zone of the ion emitter when the ion emission zone of the ion emitter is in the operative position.

The ion emission zone of the ion emitter may be reciprocally moveable between the stored position and the operative position along a substantially linear path.

The ion emission zone may be formed of a sharpened or fibrous electrically conductive element.

The sharpened or fibrous element may extend from an arm portion of the ion emitter.

The arm portion may be flexible. Therefore, it may be manoeuvred with the transfer tube so as to optimise the directionality of the ion emission zone when positioned intracorporeally.

The type of propellant depends on the desired application wherein the propellant may comprise for example a pressurised aqueous solvent (for the delivery of liquid particles), or pressurised air or carbon dioxide (for the delivery of solid particles). The particles may comprise a therapeutic agent or a diagnostic agent.

The transfer tube may be releasably attached to the main body enabling other instruments to be applied to the surgical spray instrument.

The main body may comprise a port for receiving a cartridge containing the particulate material containing propellant to be applied.

The main housing may further comprise a compartment for storing pressurised fluid for enabling propulsion of the particulate material.

The pressurised fluid may be $CO_2$ gas or air. Alternatively, the pressurised fluid may be saline or water.

In a further aspect of the invention there is provided a surgical spray instrument assembly for directing a particulate material containing propellant to a surgical site, the assembly may comprise the surgical spray instrument according to an aspect of the invention and a DC voltage electrical source, the ion emitter of the surgical instrument being electrically couplable with a pole of the electrical source. The other pole may be electrically connected to the patient.

In a further aspect of the invention there is provided a method of directing a particulate material containing propellant to a surgical site comprising use of the surgical spray instrument of according to an aspect of the invention, the method may comprise the steps in any suitable order, of:
  a) actuating release of a propellant from the main body;
  b) transferring the propellant that contains the particles to be delivered along the transfer tube to its distal end;
  c) releasing the propellant;
  d) initiating the emission of ions from the ion emission zone of the ion emitter to thereby ionise the particulate material contained within the released propellant and attract the particulate material towards the surgical site.

The method may further comprise deploying the ion emission zone of the ion emitter.

The emission of ions may be initiated subsequently to moving the ion emission zone of the ion emitter from the stored position to the operative position.

Whilst the invention has been described above it extends to any inventive combination of the features set out above, or in the following description, drawings or claims. For example, any features described in relation to any one aspect of the invention is understood to be disclosed also in relation to any other aspect of the invention.

The surgical spray instrument and surgical spray instrument assembly facilitate a directional spray of the particulate material containing propellant to the intracorporeal site of interest in a reproducible and reliable manner, thereby optimising the contact of the particles with the site. However, since the electric field lines are more concentrated in the region adjacent the shortest path between the positively and negatively charged object (i.e. the ion emission zone of the ion emitter and the patient), the propellant is preferentially applied to a localised region.

Whilst this localised deposition of the propellant may be suitable for certain surgical applications, there are occasions where homogenous deposition on the internal surface of the cavity in its entirety is required and in such instances a uniform deposition is desired. Whilst it is feasible to use multiple ion emitters with a deposition device in order to obtain a uniform coverage for a first cavity shape (whereby the positioning is usually determined using a trial and error technique), the same ion emitter positioning may not be sufficient to obtain the desired coverage of a cavity having a different topography. Therefore, this trial and error technique must be repeated in order to obtain the correct ion emitter positioning and in some instances the optimal positioning may never be achieved. Use of a trial and error positioning technique is time consuming and can lead to complications, for example internal bleeding for the patient.

Therefore, the present invention and its embodiments are intended to address at least some of these above described problems and desires. In particular, it facilitates the uniform deposition of a therapeutic or diagnostic agent on the internal wall of an abdominal cavity, regardless of the topography of the cavity.

According to a further aspect of the invention there is provided a surgical assembly for enabling uniform deposition of a particulate material to a surface of an intracorporeal cavity of a patient, the assembly comprising:

an ion emitter having at least one ion emission zone locatable within the cavity;

a dispenser having an outlet locatable within the cavity and for dispensing the particulate material therefrom, and a processor for determining a location of the at least one ion emission zone of the ion emitter in dependence upon the position of the outlet of the dispenser within the cavity to provide for the uniform deposition.

The particulate material may be a therapeutic agent or a diagnostic agent.

The position of the ion emission zone of the ion emitter may be dependent upon an electrical potential field which is capable of providing uniform deposition of the particulate material.

The processor of the assembly may also determine the location of the ion emission zone of the ion emitter in dependence upon the topography of the cavity.

At least two ion emitters may be positionable at spaced apart regions which are arranged between the outlet of the dispenser and a surface of the cavity.

The assembly may further comprise a power supply per ion emitter. Alternatively, the assembly may further comprise a common power supply for providing power to the at least two ion emitters. In this latter case, there may be included a controller for selectively powering the at least two ion emitters.

An outer surface of the ion emitter may compliment the surface of the cavity.

In a further aspect of the invention, there is provided a method of enabling uniform deposition of a particulate material to a surface of an intracorporeal cavity within a patient, the method comprising the steps in any suitable order, of:

a. determining the topography of the surface;

b. determining an electrical potential field distribution within the cavity for enabling the deposition of the particulate material in dependence upon a location of an outlet of a dispenser within the cavity and the topography of the surface, c. determining a position of at least one ion emitter within the cavity so as to generate the determined electrical potential field distribution; and d. positioning the at least one ion emitter in the determined position.

The method of enabling uniform deposition of a therapeutic or diagnostic agent to a surface of an intracorporeal cavity within a patient may further comprise the particulate material from the outlet of the dispenser. The particulate material may be therapeutic or diagnostic agents.

The method of enabling uniform deposition of a therapeutic or diagnostic agent to a surface of an intracorporeal cavity within a patient may further comprise selectively generating the electrical potential field distribution in dependence of the dispensed particulate material.

Whilst the invention has been described above it extends to any inventive combination of the features set out above, or in the following description, drawings or claims. For example, any features described in relation to any one aspect of the invention is understood to be disclosed also in relation to any other aspect of the invention.

The invention will now be described, by way of example only, with reference to the accompanying drawings, in which.

Figure 5A:
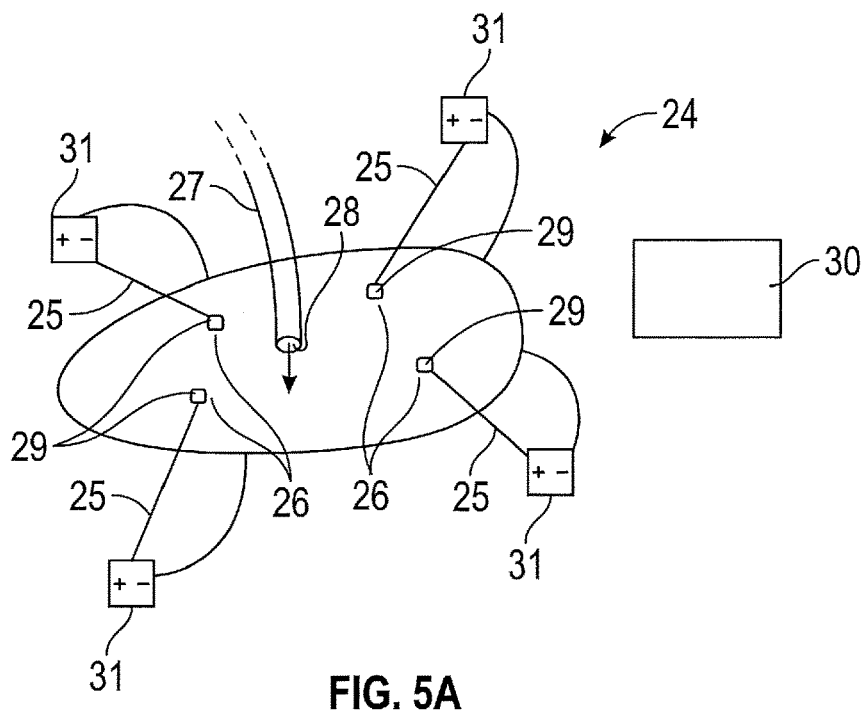
Figure 5B:
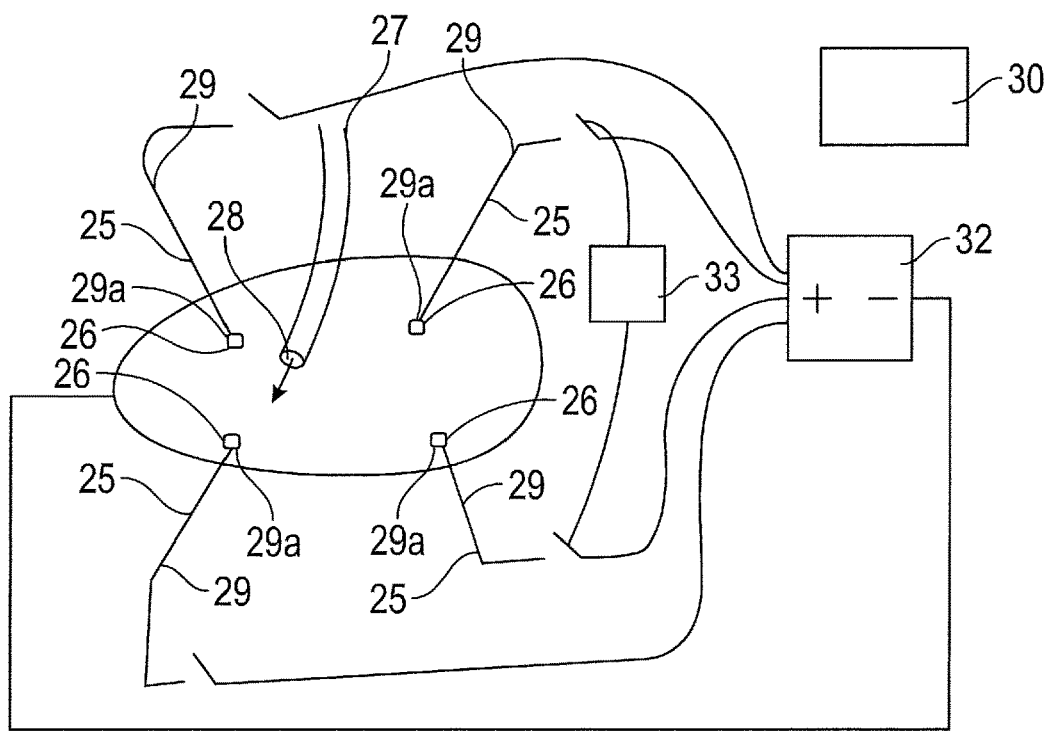
Figure 6:
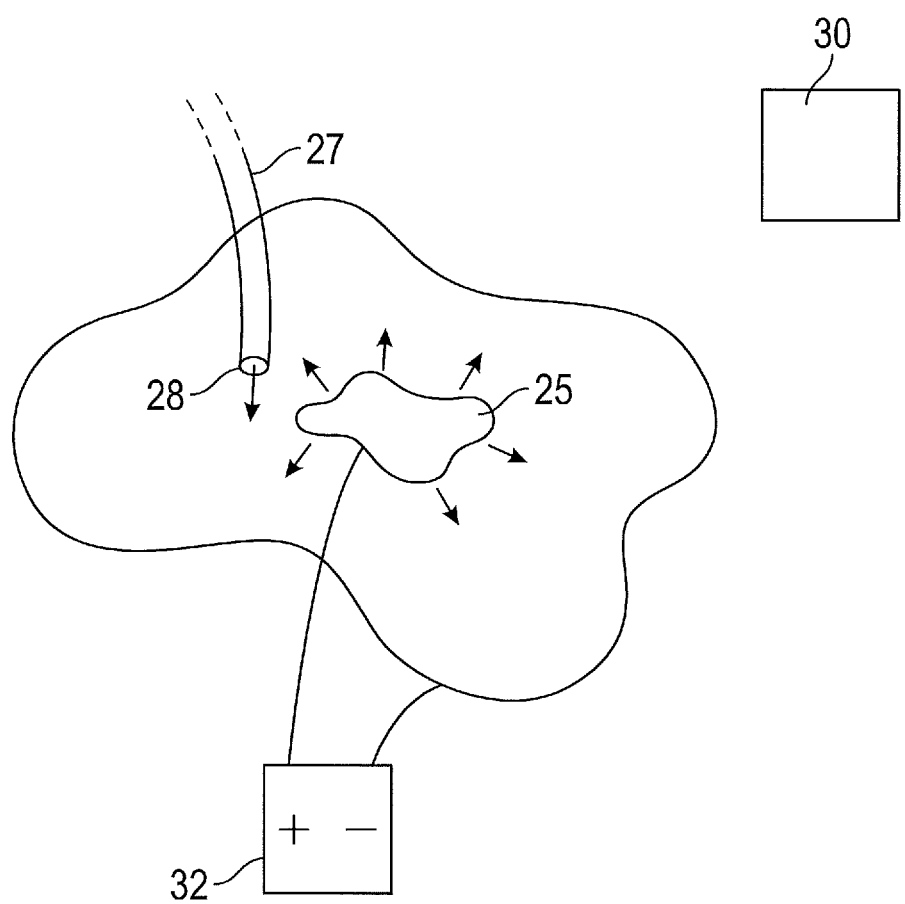

FIG. 5*a* is a schematic of the electrosurgical assembly having multiple ion emitters with separate power supplies;

FIG. 5*b* is a schematic of the electrosurgical assembly having multiple ion emitters with a common power supply; and FIG. 6 is a schematic view of the surgical assembly having a single ion emitter complimenting the shape of the patient cavity.

Figure 1:
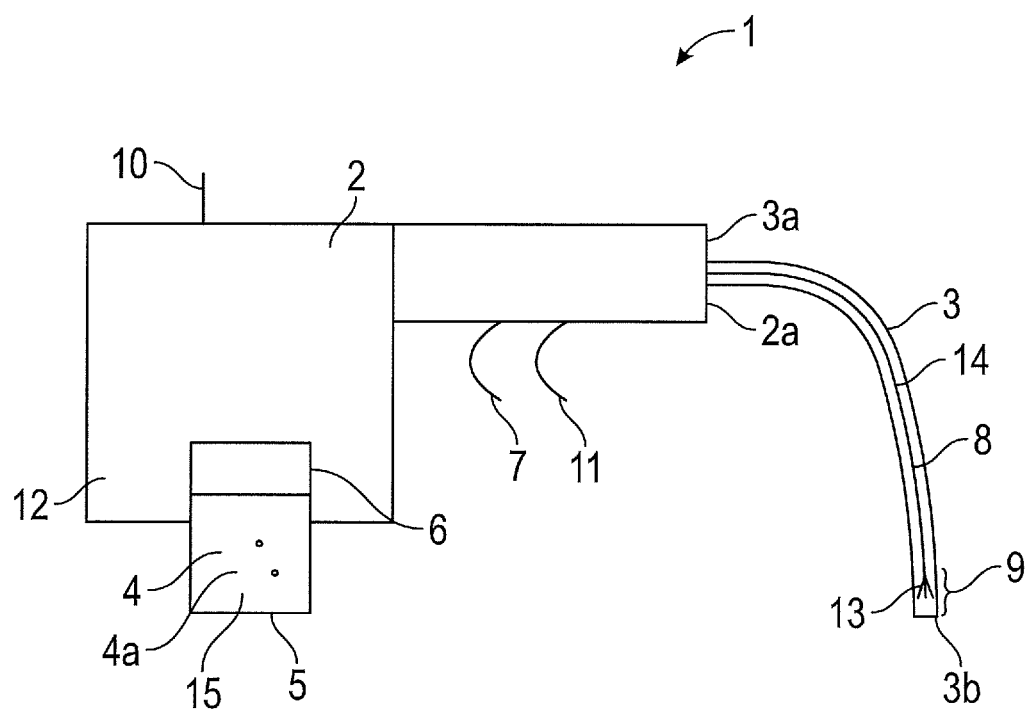
FIG. 1 is a schematic view of the surgical spray instrument with the ion emitter in a stowed state.

Referring firstly to FIG. 1, there is shown a surgical spray instrument 1 having a main body 2 which at its distal end 2*a* is connectable to a proximal end 3*a* of a transfer tube 3. The distal end 3*b* of the transfer tube 3 is positionable by a surgeon intracorporeally of a patient. A propellant 4 is contained within a cartridge 5 inserted into a port 6 of the main body 2. A propellant actuator 7 is provided for selectively releasing propellant 4 from the cartridge 5 and through the main body 2 and along the transfer tube 3 to the distal end 3*b* thereof. An ion emitter 8 is arranged along the transfer tube 3, e.g. along the interior of the transfer tube 3.

Figure 2:
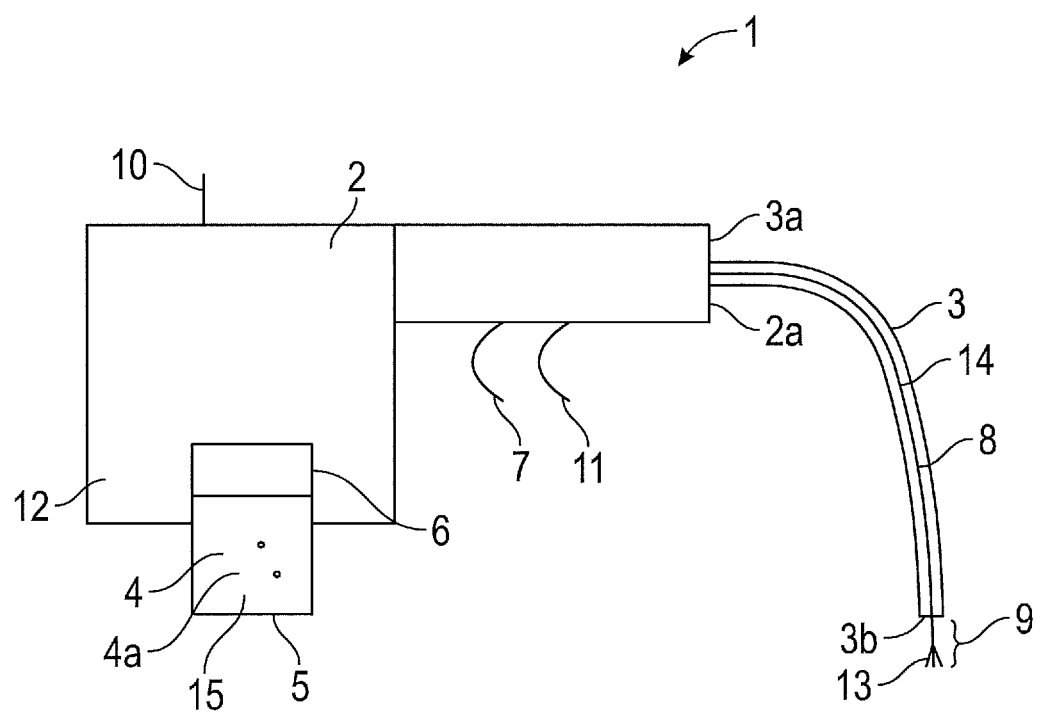
FIG. 2 is a schematic view of the surgical spray instrument with the ion emitter in an operative state.

The ion emitter 8 has an ion emission zone 9 which is projectable from the distal end 3b of the transfer tube 3. The ion emission zone 9 of the ion emitter 8 is moveable between a stowed position as shown in FIG. 1, to an operative position as shown in FIG. 2. Therefore, the ion emission zone is reciprocally moveable between the two positions along a substantially linear path.

In the stowed position of FIG. 1, the ion emission zone 9 of the ion emitter 8 is retracted within the transfer tube 3 however, in the operative position of FIG. 2, the ion emission zone 9 of the ion emitter 8 is projected from the distal end 3a of the transfer tube 3.

An ion emitter actuator 10 is provided for actuating deployment of the ion emitter 8 from the stowed position to the operative position. A further actuator 11 is applied to actuate the emission of ions from the ion emission zone 9 of the ion emitter 8 when the ion emission zone 9 of the ion emitter 8 is in the operative position.

Each of the actuators 7, 10, 11 are arranged to be controlled from a position external to the main body 2 such that when the main body 2, which has a handle portion 12, is held by the surgeon he can easily access and apply each of the actuators. The actuators 7, 10, 11 are applied by means of a trigger arrangement or an electrical switch.

The ion emission zone 9 is formed of a sharpened or fibrous element 13, which extends from an arm portion 14 of the ion emitter 8. The arm portion 14 is flexible such that it can bend in line with the transfer tube 3.

The propellant 4 comprises particles relevant to the particular application of the surgical spray instrument. In the case where a drug treatment is to be applied, the particles will be the relevant drug particles. For example, in the case where the spray is applied to help with clotting of a GI bleed, the propellant comprises a haemostatic agent. In the case where an internal region is to be observed, the propellant comprises a dye. Therefore, there are many applications for which the surgical spray instrument may be used.

The transfer tube 3 may be an integral element of the instrument, or it may be releasably attached to the main body 2 via a hollow protrusion. This removable nature of the transfer tube 3 would allow other transfer tube accessories to be applied.

The cartridge 5 to be applied to the port 6 located in the main body 2 contains a pressurised fluid 15 e.g. $CO_2$ in addition to the particles 4a to be propelled. On actuation of the propellant actuator 7, the mixed pressurised fluid 15 and particle 4a propellant are released into the main body 2 of the surgical spray instrument 1 prior to entering the transfer tube 3.

Figure 3:
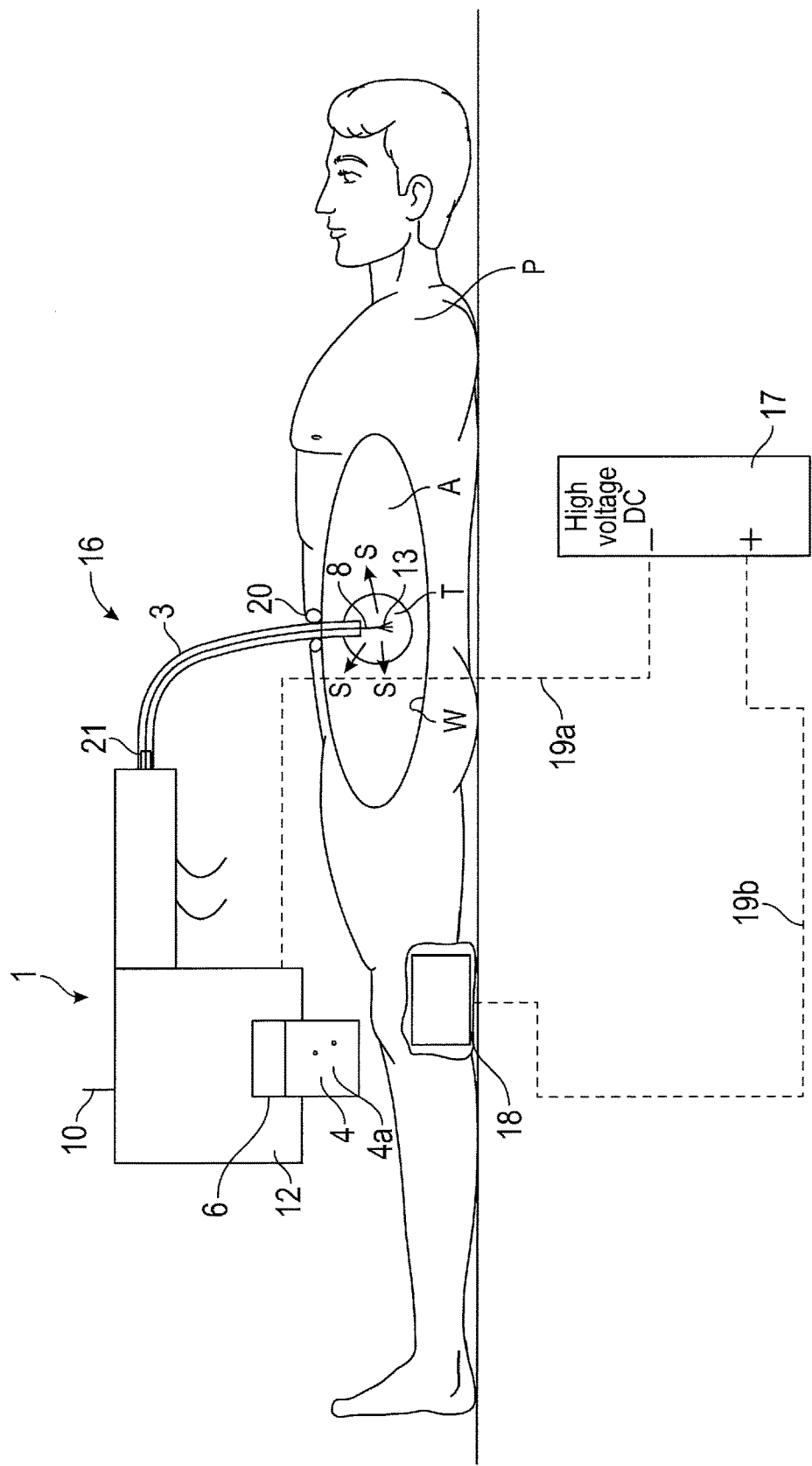
FIG. 3 is a schematic view if the surgical spray instrument assembly in an operative state applied to a patient.
Figure 4:
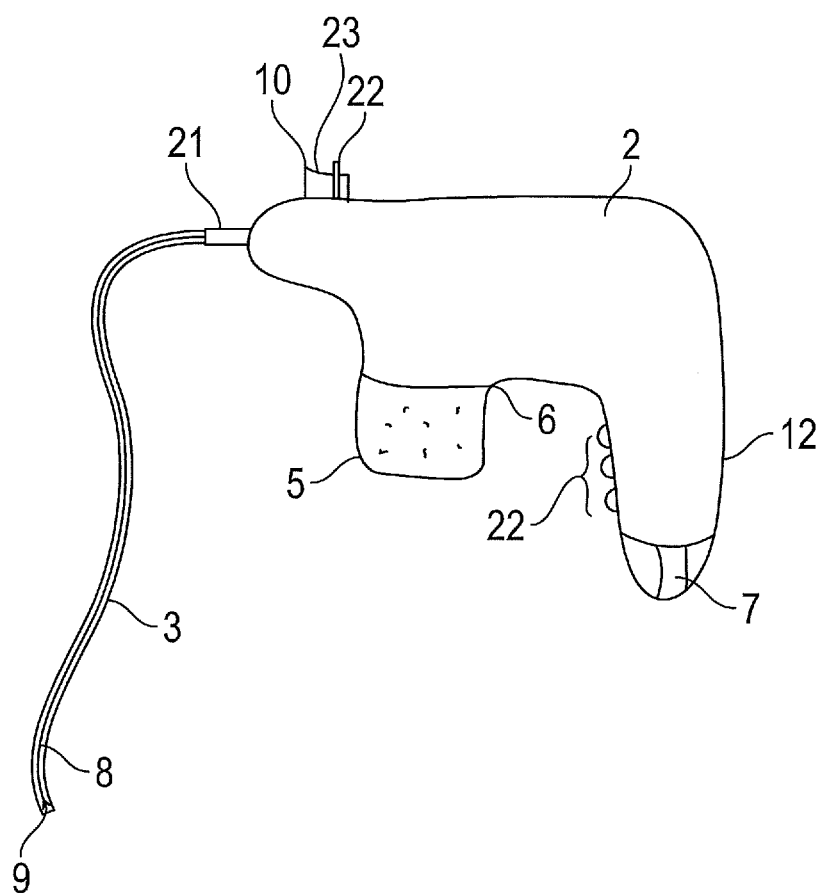
FIG. 4 is a schematic view of the surgical spray instrument.

In FIG. 3 there is shown a surgical spray instrument assembly 16 for directing propellant to an intracorporeal site, the assembly 16 comprises the surgical spray instrument 1 as described above and a DC voltage electrical source 17, the ion emitter 8 of the surgical spray instrument 1 being electrically couplable with a pole of the electrical source 17. The other of the poles is electrically connected to the patient P. An ion receiver is provided as a conductive pad 18 that is to be applied to the patient. Although for convenience the DC source 17 may be integrated as part of the instrument 1.

In use, the conductive pad 18 of the second ion emitter is attached to the leg of the patient P, or other body part, using a conducting gel and is electrically connected to the a pole, such as a positive pole of the high voltage source by means of a conductor 19*b*. The conductor 19*b* is insulated to prevent the conductor accidentally touching against the patient. The body of the patient then becomes positively charged.

The ion emitter 8 is connected to the other pole, such as the negative pole of the high voltage source via a conductor 19*a*. The ion emitter 8 is then inserted into the, for example, abdomen A through a bespoke entry device 20 or a conventional laparoscopic access port. On actuation of the ion emitter actuator 10, the ion emission zone 9 of the ion emitter 8 is moved from the stowed position, to the operative position.

Once the ion emission zone 9 has been deployed into the operative position, the further actuator is applied to cause the ion emitter 8 to become negatively charged so as to send a stream of electrons towards the intracorporeal site i.e. target zone, for example wall W of a patient's body. The electrons attach themselves to some of the suspended propellant causing the atoms in the particles to form negative ions and to become positively attracted towards the positively charged contact zone e.g. walls W of the abdomen A, where they stick thereto as desired.

Therefore, the propellant is directed towards the surgical site (e.g. an intracorporeal site) by applying the above-mentioned surgical spray instrument 1 and using a method comprising the steps, in any suitable order, of:

a) actuating release of a propellant 4 from the main body 2;
b) transferring the propellant 4 along the transfer tube 3 to its distal end 3*b;*
c) releasing the propellant 4 intracorporeally;
d) deploying the ion emission zone 9 of the ion emitter 8;
e) initiating the emission of ions from the ion emission zone 9 of the ion emitter 8 to thereby ionise said intracorporeally released propellant 4 and attract particles 4*a* in the propellant 4 towards the intracorporeal site.

The emission of ions is initiated subsequently to moving the ion emission zone 9 of the ion emitter 8 from the stowed position to the operative position. To maximise the directivity of the particles in the propellant 4 to the intracorporeal site of interest the distal end 3*b* of the transfer tube 3 must be pointed towards and adjacent to the site. A spray of propellant 4 is released from the distal end 3*a* of the transfer tube 3 towards the site and the particles in the propellant are then ionised once the ion emission zone 9 is activated.

In FIG. 4, the main body 2 and the handle 12 are an integrated unit. A connector portion 21 extends from the front end of the main body 2 and is capable of receiving the proximal end 3*a* of a transfer tube 3. A first propellant actuator is located at the base of the handle and is arranged to activate the $CO_2$ cartridge. The $CO_2$ cartridge is received in a port 6 located in the main body 2 and is substantially adjacent to the handle 12. The actuation switch of the propellant actuator is rotatable from an open to a closed position about the longitudinal axis of the handle 12. In the open position, $CO_2$ from the cartridge is permitted to flow to a region of less pressure due to the creation of a pressure differential. A portion of the outer surface of the handle 12 has a ridged profile 22 so as to improve the gripping capability of the surgeon. A valve (not shown) is positioned at the junction of the main body 2 and the transfer tube 3. The valve actuator 23 comprises a pivotable lever that can be rotated about its pivot point 22 between an open and closed position. When the open position is initiated the $CO_2$ is permitted to pass from the main body 2 to the transfer tube 3. The ion emitter actuator 10 deploys the ion emitter 8 and is used to initiate the generation of electrons from the ion emission zone 9.

The cartridge 5 has an insulator surface so as to prevent the cartridge from becoming negatively charged on electrical connection between the ion emitter and the high voltage power source. This is achieved by providing a plastic cap around the cartridge (not shown) or making the cartridge out of a plastic.

Various modifications to the principles described above would suggest themselves to the skilled person. For example, the particles 4*a* to be propelled and the pressurised fluid 15 may not be mixed in the same cartridge 5 and may instead be provided in separate cartridges whereby the mixing of the fluid and the particles to be applied intracorporeally or extracorporeally may occur in the main body 2 of the instrument, in the transfer tube 3, or in the localised atmosphere in the patient.

In a further alternative, the pressurised fluid 12 e.g. pressurised gas may be stored in an external container (not shown) and applied by means of a second transfer tube (not shown). In this arrangement, the pressurised gas will pass through the particles stored in the main body 2 to be applied and carry them through the transfer tube 3.

The triggers may not be used as the switching means, for example a rotating switch may be implemented in the handle, or a pivotable bar may be applied to the outer surface of the main body 2 to facilitate the opening and closing of a valve.

The positions of the actuators may vary as desired.

Alternatively to the ion emitter 8 passing along the interior of the transfer tube 3, it may instead be positioned along the exterior of the tube, but in such an arrangement it would be important for the ion emitter to be electrically insulated.

Alternatively, the surgical spray instrument need not be deployed at all since enough negative ions may be generated by the passage of the particulate/vapour suspension over the surgical spray instrument as it exits.

The surgical spray device may be applied extracorporeally as well as intracorporeally.

In a further embodiment of the invention the particles to be propelled by the pressurised fluid may be drug particles, for example to be applied to a cancerous or other body site.

The surgical spray instrument assembly may be a self-contained unit which comprises the high voltage source and a local battery. The required run time is quite short, therefore the capacity of a larger generator is not required. The generator located within the main body of the surgical spray instrument, for example which is located in a handle thereof, is akin to a camera flash, albeit current limited and with a higher voltage output. A small patient electrode connection would still be required in order to establish the electrical circuit, but this set up prevents the need for an electrode cable extending from the operating table.

The transfer tube 3 may be flexible or may instead be a rigid shaft so as to hold the outlet thereof in the preferred position to locally launch the propellant. Further, the transfer tube 3 has a bore that is sized to allow insertion without a port in which case the patient return electrode pathway would be achieved by applying a proximally conductive section to the surface of the transfer tube 3. Alternatively, a slideable collar electrode or a custom trocar sleeve may be implemented.

In a further alternative, the process of actuating the ion energy source may be used to generate the electrostatic charge, for example via triboelectric charge generation. Alternatively, the energy source for the high voltage circuit may be provided via electromagnetic induction, making the battery redundant. For example, the actuator may be arranged to move a coil relative to the magnetic field of a permanent magnet, which results in a current flow in a coil. Either the coil or the magnet may be caused to move to cause the current generation. This latter arrangement simplifies the re-sterilisation or high level disinfection of the spray instrument, however the transfer tube 3 would remain single use due to the difficulty in cleaning.

FIG. 5*a* shows a surgical assembly 24 for enabling uniform deposition of a therapeutic or diagnostic agent to a surface of an intracorporeal cavity of a patient. An ion emitter assembly 25 having at least one ion emission zone 26 locatable within the cavity can be operated to emit negative ions therefrom.

The assembly 24 also comprises a dispenser 27 having an outlet 28 locatable within the cavity and for dispensing the particles therefrom. The ion emitter assembly 25 and the dispenser 27 are separate and distinct elements of the assembly 24. The particles or agent to be deposited is passed through the dispenser 27 to the interior of the cavity, for example the agent may be propelled into the cavity by means of a pressurised gas or fluid. The ion emitter assembly 25 and the dispenser pass through separate ports (not shown) located in the cavity wall. The port (not shown) may be a bespoke entry device or a conventional access port.

The mechanism for this targeted deposition is as described previously whereby the ion emitter arrangement is caused to be negatively charged so as to send a stream of electrons and negative gas ions towards the surface of the cavity of the patient. The patient is connected to the positive pole of the electrical circuit so as to make the patient positively charged. The electrons and gas ions transiently attach themselves to the suspended particles dispensed within the cavity causing them to be attracted towards the positively charged the tissue within the cavity, where they are deposited thereto as desired. Moreover, the potential difference between the ion emitter and the patient tissue may be used to influence the diffusion of the molecules from within an aqueous solvent to the patient tissue. For molecules that are negatively charged in the aqueous solution, the use of a negative polarity ion emitter will create an electric field that encourages the diffusion of the molecules from the aqueous solution to the surrounding tissue. Similarly, the use of a positive polarity ion emitter will create an electric field that can encourage the diffusion of molecules that are positively charged in the aqueous solvent.

To ensure that a uniform coverage of the therapeutic or diagnostic agent on the surface of the cavity is achieved, the ion emitter assembly 24 comprises multiple ion emitters 29 positioned at spaced apart regions which are arranged between the outlet of the dispenser 27 and a surface of the cavity.

A processor 30 is provided to determine a position within the cavity of the ion emission zone 26 of the ion emitter assembly 25 that would provide a uniform deposition of the therapeutic or diagnostic agent on the cavity surface. The determined position of the ion emission zone 26 is dependent upon the position of the outlet 28 of the distributor 27 also positioned within the cavity.

The topography of the internal surface of the cavity is also required to enable the processor 30 to provide the required positioning information for the ion emission zone 26 of the ion emitter assembly. This topography data can be obtained by using scanning or other monitoring techniques, for example a CAT-scan or 3d Ultrasound techniques. The processor 30 may similarly be used to create a reference library of topographies that can be used to simplify this process for determining the positioning of the ion emission zone 26 within the cavity.

Once the data on the topography of the internal surface of the cavity and the position of the outlet 28 of the dispenser 27 are available to the processor 30 it determines an electrical field potential distribution required to provide the desired uniform deposition of the therapeutic or diagnostic agent. This can be achieved using standard electric field simulation software, for example Coulomb 3D or COMSOL.

With this electrical potential profile simulated, positioning information on the ion emitter assembly 25 components required to produce the simulated potential field distribution is established. Therefore, the output of the software is ultimately coordinates or other positional information for the ion emission zones of the ion emitters. As such, the position of the ion emission zone 26 of the ion emitter assembly 25 is dependent upon the electrical potential field distribution which has been simulated.

Power is applied to the ion emitters 29 once they are in position. Once the power has been terminated the ion emitters 29 are removed from the cavity with the knowledge that a uniform deposition has been applied. Therefore, the amount of time that components of the surgical assembly 24 have to be positioned intracorporeally is minimised compared to existing methods of creating a uniform deposition.

The particulate material may be dispensed prior to, simultaneous to or subsequent to the ion generating pulse as desired. The particles comprise either a therapeutic or diagnostic agent whose homogenous delivery provides an improved performance and/or safety profile.

The ion emitters 29 may be powered by individual power supplies 31 as shown in FIG. 5a or a common power supply 32 may be applied as shown in FIG. 5a, with the ion emitters selectively powered by means of a controller 33.

The power supply 31, 32 is a DC voltage electrical source, a pole of which is electrically couplable to the ion emitter assembly. The other of the poles of the DC voltage electrical source is electrically connected to the patient via a conductive pad that is to be applied to the patient.

In use, the conductive pad of the ion receiver is attached to the leg of the patient, or other body part, using a conducting gel and is electrically connected to one pole of the high voltage source by means of a conductor. The conductor is insulated to prevent the conductor accidentally touching against the patient. The body of the patient then becomes onepole of the circuit as a result.

The ion emitter is connected to the opposite pole of the high voltage source via a conductor.

The ion emission zone is actuated by the surgeon by an actuator such that the ion emitter assembly becomes negatively charged for example, so as to send a stream of electrons and negative gas ions towards the surface of the intracorporeal cavity of the patient as described above.

Alternatively, as shown in FIG. 6, a single ion emitter 25 may be used that complements the surface topography of the cavity.

In use the topography of the cavity is ascertained. Next, the position of the outlet 28 of the dispenser 27 within the cavity is established and the processor 30 determines an electrical potential field distribution within the cavity for enabling the deposition of the therapeutic or diagnostic agent in dependence upon the position of the outlet 28 of a dispenser 27 within the cavity.

The information regarding the topography of the surface of the cavity is also used to determine the electrical potential field distribution. The position of the ion emitter 29 that generates the determined electrical potential field distribution is then obtained in the form of coordinates or other positional information. The surgeon then positions the ion emitter 29 or ion emitter assembly 25 in accordance with the established coordinates or other positional information so as to enable generation of the simulated field within the cavity of the patient. The electrical field generation is selectively generated in dependence of the dispensed agent.

Once the ion emitter assembly is in position, the surgeon actuates the dispenser 27 so as to dispense the therapeutic or diagnostic agent from the outlet 28 of the dispenser.

Various modifications to the principles described above would suggest themselves to the skilled person. For example, the electrical potential field distribution may be simulated dependent on the position of the ion emitter 29. The electrical potential field may then be used to determine the position of the outlet 28 of the dispenser 27 that will provide uniform deposition of the therapeutic or diagnostic agent on the walls of the intracorporeal cavity. Moreover, the skilled person will recognise that while the specific embodiments have been exemplified with the ion emitter being electrically coupled to the negative pole of the voltage source and the patient being electrically coupled to the positive pole, the ion emitter could alternatively be electrically coupled to the positive pole of the voltage source and the patient could be electrically coupled to the negative pole.

The invention claimed is:

1. A surgical assembly for enabling uniform deposition of a particulate material to a surface of an intracorporeal cavity of a patient comprising:
   an ion emitter having an ion emission zone locatable within the cavity;
   a dispenser having an outlet locatable within the cavity and for dispensing the particulate material therefrom, and
   a processor for determining a location of the ion emission zone of the ion emitter in dependence upon the position of the outlet of the distributor within the cavity to provide for the uniform deposition.

2. A surgical assembly according to claim 1, wherein the particulate material is a therapeutic agent.

3. A surgical assembly according to claim 1, wherein the particulate material is a diagnostic agent.

4. A surgical assembly according to claim 1, wherein the position of the ion emission zone of the ion emitter is dependent upon an electrical potential field which is capable of providing uniform deposition of the particulate material.

5. A surgical assembly according to claim 1, wherein the processor is arranged to determine the location of the ion emission zone of the ion emitter in dependence upon the topography of the cavity.

6. A surgical assembly according to claim 1, wherein at least two ion emitters are positioned at spaced apart regions which are arranged between the outlet of the dispenser and a surface of the cavity.

7. A surgical assembly according to claim 6, further comprising a power supply per ion emitter.

8. A surgical assembly according to claim 7, further comprising a common power supply for providing power to the at least two ion emitters.

9. A surgical assembly according to claim 8, further comprising a controller for selectively powering the at least two ion emitters.

10. A surgical assembly according to claim 1, wherein an outer surface of the ion emitter compliments the surface of the cavity.

* * * * *